United States Patent [19]

Dumbeck, Sr.

[11] Patent Number: 4,972,081
[45] Date of Patent: Nov. 20, 1990

[54] DETECTION OF CONTAMINANTS IN AIR

[76] Inventor: Robert F. Dumbeck, Sr., P.O. Box 548, Elgin, Tex. 78621

[21] Appl. No.: 9,520

[22] Filed: Feb. 2, 1987

Related U.S. Application Data

[63] Continuation-in-part of Ser. No. 657,185, Oct. 3, 1984.

[51] Int. Cl.$^5$ .............................................. G01T 1/185
[52] U.S. Cl. .................................. 250/253; 250/380; 250/385.1
[58] Field of Search ............... 250/253, 380, 381, 382, 250/385.1, 370.4

[56] References Cited

U.S. PATENT DOCUMENTS

| | | | |
|---|---|---|---|
| 3,621,238 | 11/1971 | Jalbert et al. | 250/380 |
| 4,044,263 | 8/1977 | Ried, Jr. et al. | 250/381 |
| 4,185,199 | 1/1980 | Droullard et al. | 250/364 |
| 4,205,306 | 5/1980 | Turlej | 250/381 |
| 4,213,046 | 7/1980 | Beyersdorf | 250/381 |
| 4,262,203 | 4/1981 | Overhoff | 250/380 |
| 4,280,052 | 7/1981 | Solomon | 250/381 |
| 4,336,455 | 6/1982 | Bryant | 250/381 |
| 4,342,913 | 8/1982 | Shepherd | 250/364 |

FOREIGN PATENT DOCUMENTS 1579144 11/1980 United Kingdom .

*Primary Examiner*—Constantine Hannaher
*Attorney, Agent, or Firm*—Laurence R. Brown

[57] ABSTRACT

A sensitive alpha radiation detector, not responsive to beta or gamma radiation, is provided in an air contamination system to respond to small levels of radon such as 4 picocuries per liter of air. Thus a substantially instantaneous detector for radon in dwellings is provided. The detector comprises a vessel having a housing outer electrode with an air passage screen leading into a first interior compartment confronting a detector electrode. Another interior compartment has therein a calibrated alpha source for ionizing that compartment which is separated from the first compartment by the detector electrode. Thus a small amount of alpha radiation is detectable when presented near the air passage screen. For providing direct radon readings consistent with the Environmental Protection Agency standard of 4 picocuries per liter of air, accumulation of dust and radon daughters from a measured amount of air passed through a filter for a minute or so are processed. Direct reading of alpha radiation is achieved substantially instantaneously.

14 Claims, 3 Drawing Sheets

DETECTION OF CONTAMINANTS IN AIR

TECHNICAL FIELD

This invention relates to means and methods for detection of contaminants in air, and more particularly it relates to the detection of the presence of small amounts of radon in air and other contaminants.

BACKGROUND ART

This is a continuation-in-part of my co-pending application U.S. Ser. No. 06/657,185 for Stale Air Detection for Dwellings, which is incorporated herein in its entirety by reference.

In that application ionization type detectors are employed to detect when oxygen levels in air fall below safe levels. A system for comparing air to be monitored as sensed by one detector with air of known quality as a reference as sensed by another detector provides a high sensitivity for reading very small variations of air contaminants.

One particular contaminant is of significant interest, namely radon gas, which is released from the soil and tends to accumulate inside houses at levels providing the risk of lung cancer comparable to that of heavy smokers. The Environmental Protection Agency has established a maximum safe level for radon at 4 picocuries per liter of air. Conventional radon detectors are not very sensitive and are very expensive, so that it is difficult to measure contemporaneously and almost instantly the radon presence in a home. Typical gathering times for detected samples to be processed in laboratory type equipment are greater than one week. Thus, there is a significant need for an instrument that may be used substantially instantly in the home for detecting the presence of radon, particularly if inexpensive and reliable in calibration with a detection sensitivity down to the range of 4 picocuries per liter of air.

The system in the foregoing application is deficient in its capability to detect radon at the desired sensitivity to low radon levels so that for example the 4 picocuries per liter radon level can be accurately ascertained in an inexpensive and substantially instantaneous detection of the presence of radon in a dwelling. It is particularly desirable also to be able to sample the local air about a seam or water pipe coming through basement wall in a search for radon presence. Thus an objective of this present invention is to provide a sensitive and rapid air contamination portable detector that will detect in situ low levels or radon.

DISCLOSURE OF THE INVENTION

This invention provides means and methods for measuring contaminants in air including low levels of radon. Thus an inexpensive portable instrument usable in situ in a dwelling to sample air and give readings of the radon level within minutes is feasible for the first time. Thus ionization changes may be detected in a manner similar to the system in the foregoing patent to indicate the presence of radon.

Quantitative measurements of radon levels with high sensitivity are made possible with the novel instrumentation and methods of this invention.

Quantitative measurement of the presence of radon at levels as low as 4 picocuries per liter of air can now be measured in time periods of less than a minute. This is achieved by use of a filter-blower system electronically calibrated for measurement of the air passing through the instrument to accumulate on the filter a radon sample of determinable magnitude. The novel instrumentation then provides the direct radon reading at the lowest significant levels of contamination, almost instantaneously.

It is essential in the detection of radon gas that alpha radiation be detected. It is also essential that the sensitivity of an instrument is great enough to detect only a few picocuries of radon per liter of air, essentially instantaneously so that long term collection of air samples in filters is not necessary.

Thus, this invention provides a novel sensitive alpha radiation detector. Many radiation detectors are not discriminatory in that they may also detect beta and gamma radiation as well as alpha radiation. Thus, other radiation contaminants could give a false indication of radon presence. The instrument provided thus is sensitive to alpha radiation, and excludes other radioactive radiation.

The alpha radiation instrument itself comprises an ionization detection chamber having therein a calibrated radioactive alpha emitter source, and a set of electrodes for determining variations in current flow when an outer shield electrode is subjected to ionization from smoke, odors and the like. In this outer shield electrode is an air passage opening which permits alpha radiation to enter the chamber and thus produce changes in the current flow as a function of the alpha radiation.

To eliminate the effect of the presence of other ionization sources which might cause errors in the reading of the alpha radiation magnitude, a similar comparison cell is provided in the general manner set forth in the aforesaid patent as a standard to test the quality of the air. Thus a comparative reading of one cell exposed to the alpha radiation and one cell exposed to the general flow of ambient air without accumulated radon radiation samples will eliminate errors due to ionization from other than the alpha radiation source.

Further features, advantages and details of the invention will be found throughout the following description as clarified by the accompanying drawings.

DETAILED DESCRIPTION OF THE DRAWINGS

Figure 1:
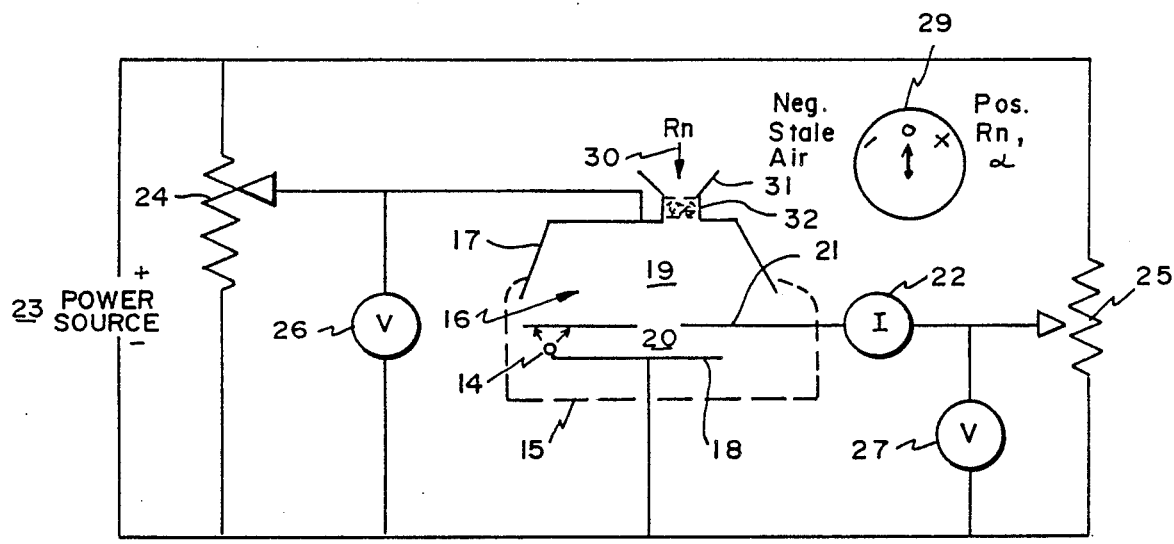
Figure 2:
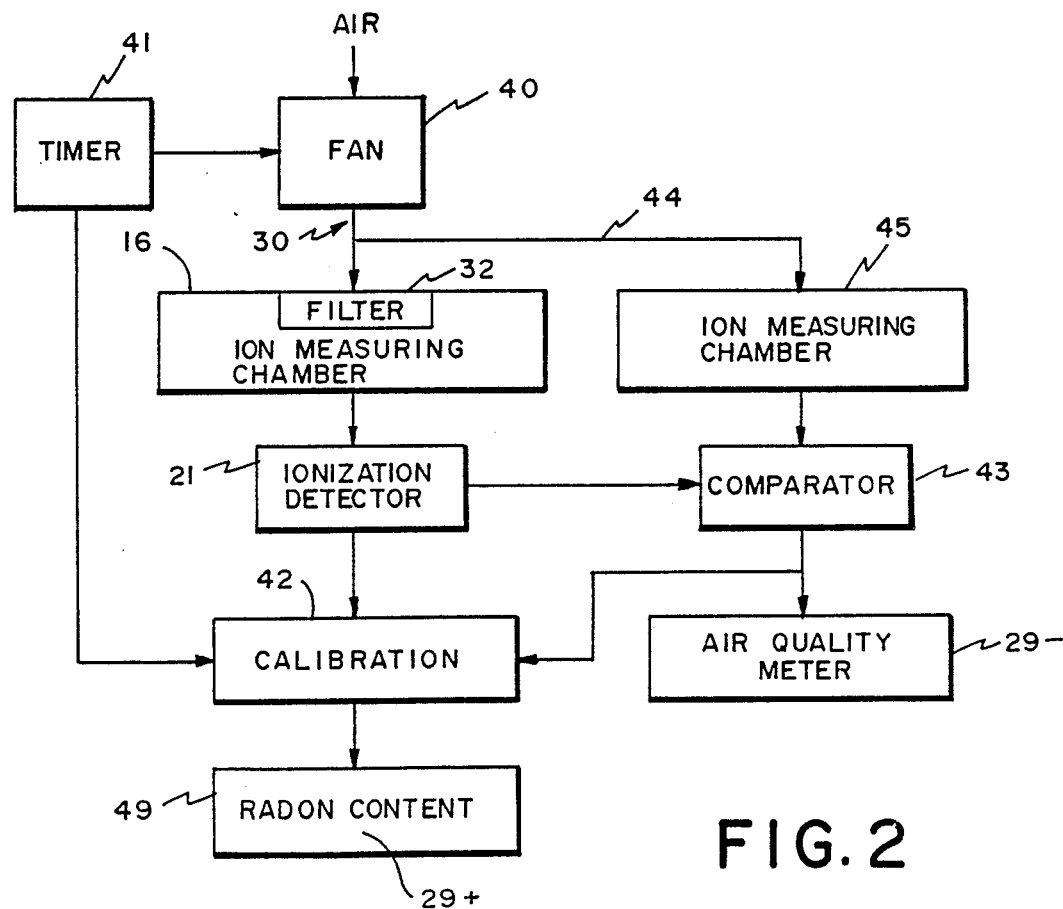
Figure 3:
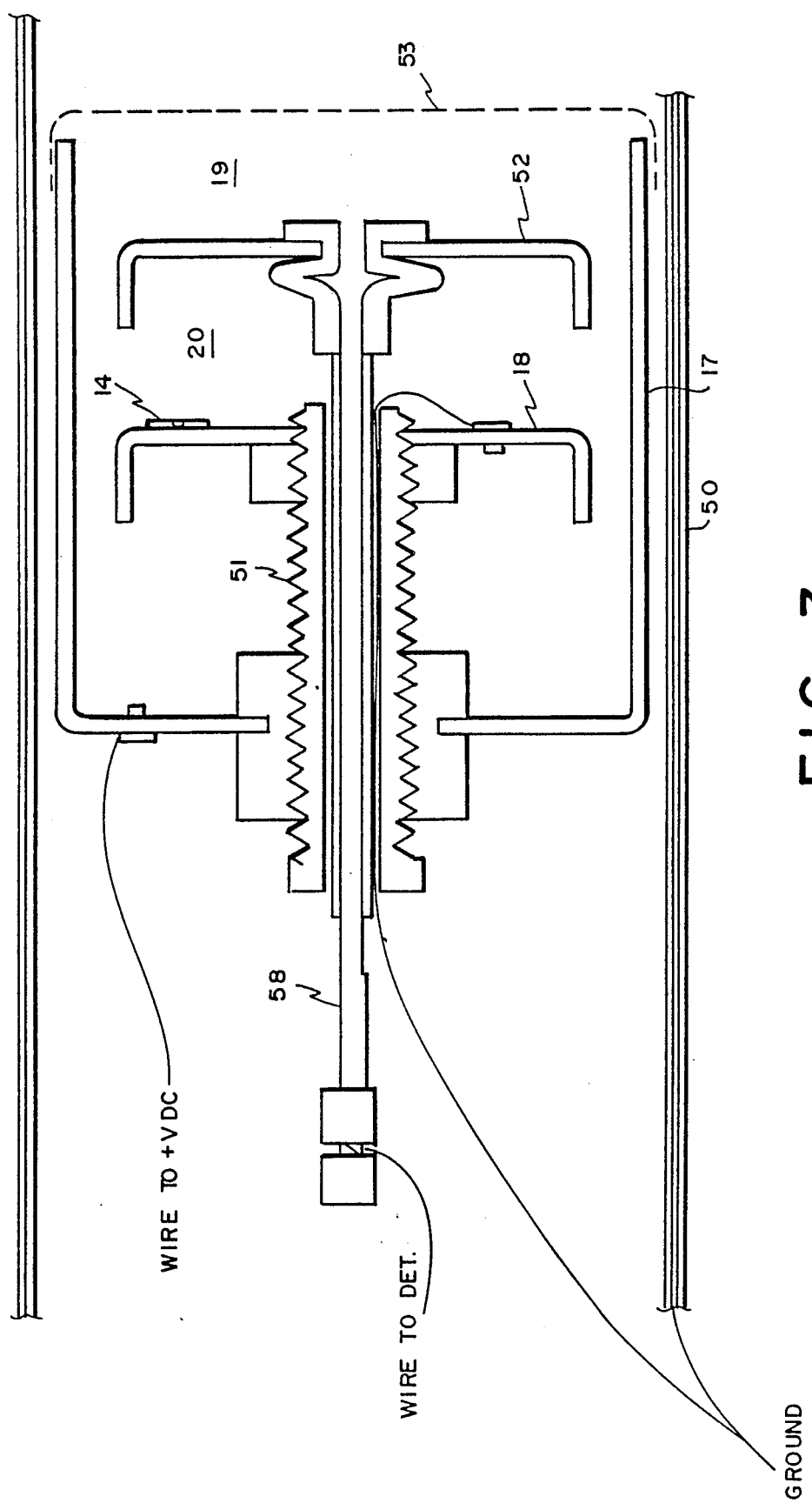
Figure 5:
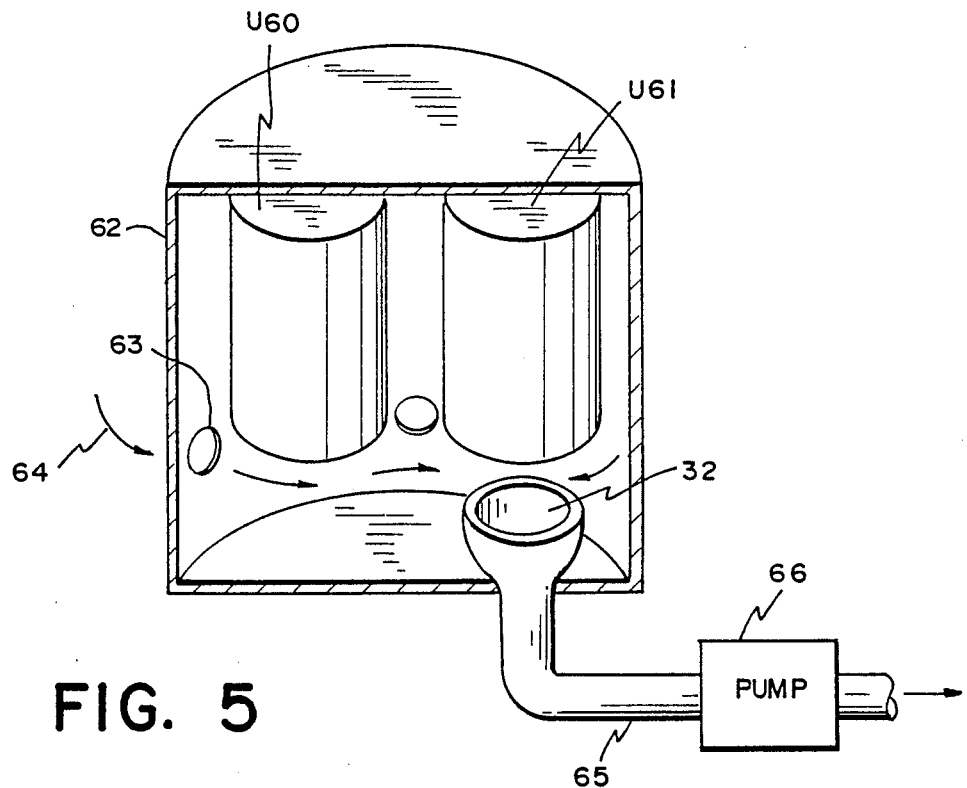
Figure 4:
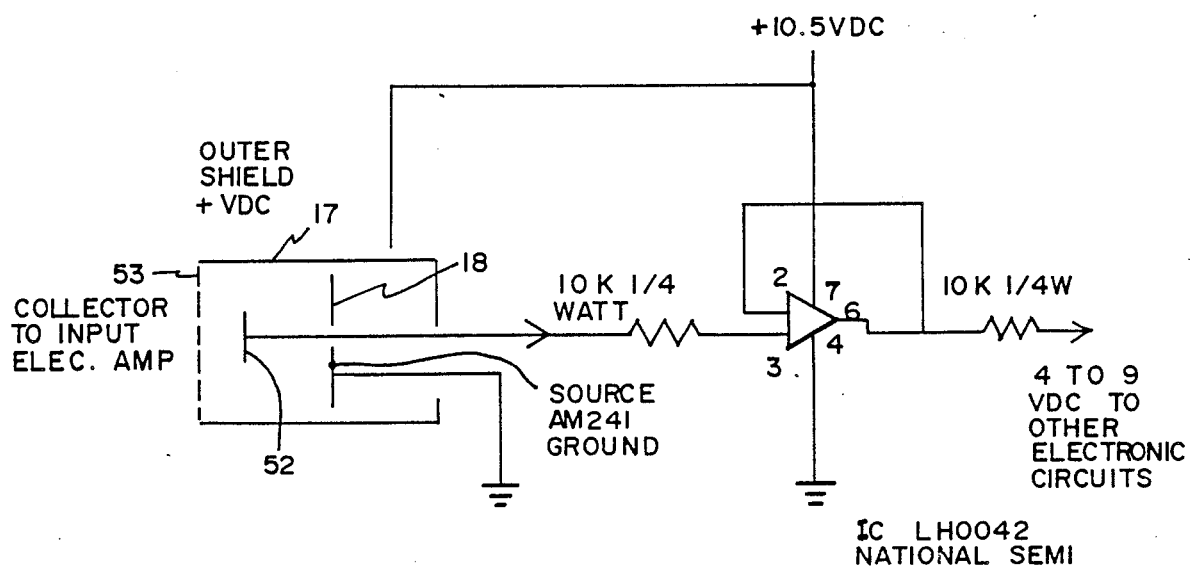

In the drawings:

FIG. 1 is a schematic diagram of radon detecting instrumentation provided by this invention, FIG. 2 is a block diagram of an instrument system for quantitative measurement of air contamination as afforded by this invention, FIG. 3 is a view across the mid section of a cylindrical alpha radiation detector cell provided by this invention, FIG. 4 is an electronic circuit schematic of the basic cell readout system, and FIG. 5 is a sketch of an alpha detector instrument adapted to measure the presence of radon gas at low levels of concentration.

THE PREFERRED EMBODIMENTS

In the detector configuration of FIG. 1, the detector contained within a vessel 15 has an ionized region confined within a chamber 16 defined by a set of electrodes 17, 18, which is produced by an internally located radioisotope 14. The outer electrode 17 is exposed for contact with an air environment and defines a first chamber compartment 19. The inner electrode 18 defines a second chamber compartment 20. Detector electrode 21 is located within the chamber 16 for detecting an unbalance of ionization in the two compartments 19 and 20, by means of current readings at ammeter or other electronic measuring device 22 when the power supply 23 provides proper potentials for the electrodes as suggested by potentiometers 24 and 25 and voltmeters 26, 27.

The vessel 15 contains appropriate means for exposing the ionized region 16 to the influence of ambient air capable of changing the balance potential at the detector electrode 21 in response to contamination in the air. Ionization detectors operating generally on this principle are commercially available from the Amersham Company, 2836 So. Clearbrook Drive, Arlington Heights, Ill., 60005, as well as details of their operating characteristics.

In the past these detectors have been used for example as smoke detectors wherein the presence of smoke in the air will provide a negative current reaction at detector electrode 21 as suggested by a counter clockwise movement of the needle on meter face 29. Should there be radon present in the contaminated air, it however would have the opposite effect and tend to move the meter needle in the clockwise direction. That requires completely different types of electronic detection circuits responsive to either positive or negative transitions at the detector electrode. Also there is a problem of instrument sensitivity if it be desirable to substantially instantaneously produce readings of such low concentrations of radon as 4 picocuries per liter of air.

To resolve these problems the operation of the system is significantly altered by means of a radon flow 30 achieved by blowing air through the entryway 31 in which filter 32 is located within the ionized chamber 16 so that the ionization within the chamber is directly and positively affected by the added ionization contributed by the presence of radon gas or its daughters.

Accordingly the unbalances of ionization between the two compartments 19 and 20 in two opposite directions may be used for determining contaminants in the air in the matter taught in the foregoing application, and also may be used for the detection of the presence of radon in the air at low concentration levels as indicated at 29.

In this embodiment the air flow path (30) thus passes through the outer electrode 17 which defines the ionization chamber 16. The filter 32 is disposed adjacent the outer electrode in the flow of air 30 for retaining and concentrating contaminants in the flow of air therethrough. Typically the air flow is timed and measured accurately by suitable air flow speed and dimensions, over a time period such as one minute, and a reading taken will then be quantitatively related to the percentage of contamination in the air.

Accordingly a predetermined datum reading at the detector electrode 21 may be taken with a clean filter in place, the air to be monitored then being passed through the filter for the period of one minute, and the difference in the detected ionization imbalance reading from the datum reading will show the amount of cumulated contamination. By accumulating radon gas and radon daughters with dust in the air over the specified time period, much lower levels of radon may be accurately determined.

However the measurement sensitivity is significantly increased beyond any capabilities of the prior art to reach accurate measurements of levels of radon at the 4 picocuries per liter critical permissible level by means of the introduction at 31 of the radon gas as an ionization source directly into the chamber 16 to supplement that ionization from the internal calibrated source 14.

The instrumentation and method of detection is more amply set forth by reference to the system diagram of FIG. 2. In order to quantify accurately the output readings for the presence of radon, fan 40, timer 41 and air flow volume, determinable from the flow rate and the flow path dimensions, are carefully calibrated. Thus, the amount of air flow through filter 32 is known after the sampling period, so that the reading taken at detector electrode 21 will reflect the effect of the radon and its daughters in the dust on filter 32 as an auxiliary ionization source giving extreme sensitivity to the presence of very small percentages of radon radioactivity per liter of air. The calibration circuit 42 will then convert the detected reading to give the radon radioactivity content 29+ at an appropriate meter, printout or alarm device.

For the air quality reading for other air contamination such as the deficiency of oxygen set forth in the foregoing application, the reading 29− is taken from an equivalent comparator 43 as set forth therein, wherein the air flow path 44, flowing through the second detector 45 is measured and compared with the contaminated air accumulated on the filter 32.

The comparator 43 output is also used in the calibration of the radon detection by eliminating any errors caused by the reaction of the chamber to stale air ingredients such as odors and smoke present. Thus, the radon content reading at 49 is available after correction in the calibration circuit 42 to show such small magnitudes as 4 picocuries per liter of air, which is the significant threshold level of measurement for radon contamination determined by the Environmental Protection Agency.

In the method of determining the radon content per liter or air, the fan 40 may be an electronic pump operated for a predetermined time period by timer 41, at which time the magnitude of accumulated radon is measured at calibration circuit 42, as corrected for deviations by other contaminants in the air.

The physical embodiment of one cell configuration is shown in FIG. 3, where a view is taken through the center of a cylinder with the outer housing electrode 17 being one inch (2.54 cm) in diameter. The outer grounded shield 50 is a metal foil 0.003" (0.008 cm) housed between 0.003" (0.008 cm) layers of insulation of plastic such as a polyester sold under the "MYLAR" Brand.

The inner grounded electrode 18 is fixed in place relative to the outer housing electrode 17 by the mounting structure 51. Insulating portions such as the mounting screw 51 are of a plastic such as a polyamide sold under the "NYLON" brand. The metal parts are of aluminum. The sensing electrode 52 is movable axially by means of shaft 58, as a matter of adjusting the sensitivity range of the detector. The grounded electrode 18 carries the alpha radiation standard 14 which is directed into compartment 20 toward the sensing electrode 52 by means of 1/16 inch (0.16 cm) diameter hole in a cover cap of a compartment containing a one microcurie AM241 standard radiation source.

The open end shield screen 53 is of a wire mesh electrically connected with the outer electrode 17. Thus the sensitive end of the detector is at the open screen end.

The screen permits alpha radiation to penetrate the interior sensing compartment 19.

For a sensitivity enabling 4 picocurie per liter of air range, the sensing electrode 52 is placed 0.2 inch (0.5 cm) from the outer screen, with the grounded electrode 18 placed one half inch from the screen and an overall axial length of the outer electrode 17 being one inch (2.54 cm).

As seen in FIG. 4, the basic detector has internal electronics comprising an integrated circuit 1CLH0042 from National Semiconductor which provides an output range of 4 to 9 volts D.C. for use in an alarm or other types of electronic circuits for quantitative measurements.

FIG. 5 is a sketch of two cells 60 and 61 mounted in a common container 62. Eight air entry holes 63 about the container of about ⅜ inch (.9 cm) diameter are positioned to permit influx of air 64. The air passes by cell 60 and cell 61 but must exit the tube 65. A piezo electric pump 66 can thus pass air through the cells at seven cubic feet (2.1 cubic meters) per minute for a metered amount of air flow. Other calibrated fan means may be used.

In the outlet tube 65 entranceway located to face the sensing end of cell 61 is a removable, replaceable filter pad 32. It collects the radon daughters per measured increment of air, so that output readings for radon can be calibrated into microcuries per liter of air.

The electrical connections are not shown, but the cells are arranged as in the parent application to use cell 60 as a standard connected without filter 32 producing a radon source to detect the quality of the air. Thus any readings in cell 61 are adjusted and balanced out so that smoke, stale air, etc. will not cause errors in the radon readings.

This cell in operation has been found to reject radioactive radiation other than alpha radiation and thus constitutes a selective alpha radiation meter. Since radon daughters are identified through their alpha radiation, therefore this instrument provides a substantially instantaneous response to the presense of alpha radiation. It further detects the very low concentration levels of alpha radiation such as 4 pico curies per liter of air that need be detected to determine compliance with safety standards in residences.

Delays of one or more minutes are necessary in order to collect and determine the presence of the amount of radon per unit of air passing through the instrument, but substantially immediate response to the presence of radon gas is detected whenever the radon daughters are collected upon the filter.

It is seen therefore that this invention has improved the state of the art by providing novel instrumentation and methods of detection of contaminants in air and in particular has provided novel and improved means and methods of detecting the presence of radon in air. Therefore those features of novelty descriptive of the nature and spirit of the invention are set forth with particularity in the appended claims.

I claim:

1. Instrumentation for detecting the presence of alpha radiation, comprising in combination.
    a vessel containing an ionized region confined within a chamber defined by a set of electrodes comprising an outer electrode exposed for contact with an air environment defining a first chamber compartment, an inner electrode defining another chamber compartment, a detector electrode located between the compartments within the vessel for detecting an unbalance of ionization between the two compartments, and a radioactive source in the vessel for producing ionization in one compartment as to establish a predetermined balance potential at the detector electrode when a predetermined potential is coupled between the outer and inner electrodes.
    means for exposing the detector electrode to the influence of alpha radiation being monitored which is capable of determining changes in the balance of ionization between the chambers as determined by the detector electrode, and means for exposing the detector electrode to a measured volume of air.

2. Instrumentation as defined in claim 1 wherein the means for exposing the detector electrode to the influence of alpha radiation comprises said outer electrode which substantially surrounds the detector electrode and has openings therein for entry of air and alpha radiation into a compartment adjacent the detector electrode.

3. Instrumentation as defined in claim 1 including means for calibrating the response of the detector electrode to determine alpha radiation per unit of air volume.

4. Instrumentation as defined in claim 3 including filter means for accumulating radon daughters from said volume of air located to expose the detector electrode to alpha radiation therefrom.

5. Instrumentation for detecting the presence of alpha radiation, comprising in combination,
    a vessel containing an ionized region confined within a chamber defined by a set of electrodes comprising an outer electrode exposed for contact with an air environment defining a first chamber compartment, an inner electrode defining another chamber compartment, a detector electrode located between the compartments within the vessel for detecting an unbalance of ionization between the two compartments, and a radioactive source in the vessel for producing ionization in one compartment as to establish a predetermined balance potential at the detector electrode when a predetermined potential is coupled between the outer and inner electrodes,
    means for exposing the detector electrode to the influence of alpha radiation being monitored which is capable of determining changes in the balance of ionization between the chambers as determined by the detector electrode,
    and means for exposing the detector electrode to a measured volume of air,
    a second vessel of similar characteristics, means for introducing ambient air into one vessel and alpha radiation into the other vessel, and
    means for comparing responses from the two vessels to isolate the effect of alpha radiation from other air contaminants affecting the detector electrode.

6. An air contamination detector comprising in combination,
    a vessel containing an ionized region confined within a chamber defined by a set of electrodes comprising an outer electrode exposed for contact with an air environment defining a first chamber compartment, an inner electrode defining a second inner chamber compartment, a detector electrode located between the compartments, an ionization source located in the inner chamber including a current flow between said electrodes, aperture means in the outer electrode exposing the first chamber and the detector electrode to air and alpha radiation present in the air so as to change the current flow at the detector electrode in response to the alpha radiation present in the air, means for passing a measurable flow of air past said aperture means, and means for calibrating the detector electrode to produce a readout per unit volume of air flow.

7. An air contamination detector as defined in claim 6 having a filter for collecting particles in the air located adjacent said aperture means to direct any radioactive alpha radiation therefrom into said first chamber.

8. Instrumentation as defined in claim 7, further comprising
    means for passing air through said filter for a predetermined period of time
    determining the influence on ionization within the compartments effected by the presence of contaminants on the to collect thereon particles in air which emit radioactive alpha radiation so as to modify current flow between said electrodes produced by the ionization source.

9. Instrumentation as defined in claim 8
    means for producing an output indication from current flow through the detector electrode in response to alpha radiation from said filter at the end of the time period, and
    means for calibrating the output indication for indicating a level of radon gas in the air flow passing through the filter for said time period.

10. Instrumentation as defined in claim 8 further including
    means for establishing a predetermined datum reading of the detected ionization condition in the two compartments with the filter in place, and
    means for determining from the detected ionization condition in the two compartments in response to radiation collected on the filter the difference in the detected ionization condition from the datum reading.

11. An air contamination detector as defined in claim 6 adapted to detect alpha radiation by combination of two like detectors, means for passing the same air flow past both detectors, means positioning a filter for collecting radon daughters adjacent the aperture means in only one detector, and means for calibrating the reading of the detector adjacent the filter to eliminate air contamination readings from the other detector.

12. The method of detecting contaminants in air comprising the steps of:
    providing a chamber for receiving air to be monitored having a calibrated alpha radiation source and a set of electrodes therein coupled to detection means responsive to produce a current flow varying with differences in ionization conditions within the chamber,
    providing an air flow path into said chamber introducing alpha radiation thereinto for affecting the ionization condition at said detection means in the presence of ionization in the air, as to monitor air that affects the ionization within the chamber,
    measuring changes in the ionization within the chamber responsive to the alpha radiation in the air being monitored, collecting over a measured time interval contaminants in the air flow path in a filter exposed to the ionization chamber,
    determining the presence and magnitude of contaminants in the air being monitored from the differences in ionization within the chamber caused by contaminants on the filter, and
    calibrating from changes in ionization within the chamber the magnitude of alpha radiation in the air flowing through the filter.

13. The method of claim 12 including the step of providing from the changes in ionization a quantitative measure of the radon contamination level per liter of the air being monitored.

14. The method of detecting the presence of radon in air comprising the steps of:
    concentrating contaminants in a measured flow of air through a filter for a predetermined time interval,
    comparing alpha radiation in the filter with alpha radiation from a calibrated source by measuring ionization changes induced in a chamber containing said source as induced by said filter as an indication of the presence of radon,
    and calibrating the measured ionization changes as a function of the air flow interval to produce a quantification of the radon level per unit of the air flowing through the filter.

* * * * *